(12) United States Patent
Kis et al.

(10) Patent No.: US 9,333,225 B2
(45) Date of Patent: May 10, 2016

(54) ONCOLYTIC VIROTHERAPY FOR THE THERAPY OF EWING'S SARCOMA

(71) Applicant: DEUTSCHES KREBSFORSCHUNGSZENTRUM, Heidelberg (DE)

(72) Inventors: Zoltan Kis, Salaj (RO); Jeaninne Lacroix, Heidelberg (DE); Barbara Leuchs, Heidelberg (DE); Monika Frank-Stohr, Neckargerach (DE); Jorg Schlehofer, Leimen (DE); Jean Rommelaere, Heidelberg (DE)

(73) Assignee: DEUTSCHES KREBSFORSCHUNGZENTRUM, Heidelberg (DE)

( * ) Notice: Subject to any disclaimer, the term of this patent is extended or adjusted under 35 U.S.C. 154(b) by 0 days.

(21) Appl. No.: 14/105,599

(22) Filed: Dec. 13, 2013

(65) Prior Publication Data

US 2014/0205573 A1    Jul. 24, 2014

Related U.S. Application Data

(63) Continuation-in-part of application No. PCT/EP2012/002539, filed on Jun. 15, 2012.

(30) Foreign Application Priority Data

Jun. 15, 2011 (EP) .................................. 11004884

(51) Int. Cl.
*A61K 35/768* (2015.01)
*C12N 7/00* (2006.01)

(52) U.S. Cl.
CPC ................ *A61K 35/768* (2013.01); *C12N 7/00* (2013.01); *C12N 2750/14332* (2013.01)

(58) Field of Classification Search
None
See application file for complete search history.

(56) References Cited

U.S. PATENT DOCUMENTS

2004/0087531 A1* 5/2004 Telerman et al. ............... 514/44
2008/0057037 A1* 3/2008 Roberts et al. ............... 424/93.6

OTHER PUBLICATIONS

Toolan et al., Proc Soc Exp Biol Med, 1965;119:711-715.*
Rommelaere et al., Cytokine & Growth Factor Reviews, Apr.-Jun. 2010, 21(2-3):185-195.*
Schwarzbach et al., (International Journal of Oncology, 2002, 20:1211-1218.*
Mutlu D et al: 54 A prospective study of Parvovirus B19 infections in pediatric solid-organ and bone marrow transplant recipients and pediatric solid tumor patients: Preliminary results, International Journal of Infectious Diseases International Society for Infectious Diseases Hamilton CA vol. 10 Jan. 1, 2006 p. S30.
Giese Nathalia A et al: Suppression of metastatic hemangiosarcoma by a parvovirus MVMp vector transducing the IP-10 chemokine into immunocompetent mice Cancer Gene Therapy May 2002 vol. 9 No. 5 May 1, 2002 pp. 432-442.
Office action for Japanese Patent Application No. 2014-515098.
English translation of office action for Japanese Patent Application No. 2014-515098.

* cited by examiner

*Primary Examiner* — Nicole Kinsey White
(74) *Attorney, Agent, or Firm* — Vedder Price P.C.; Thomas J. Kowalski; Deborah L. Lu (57) ABSTRACT

The present invention relates to a parvovirus for the treatment of mesenchymal tumors, preferably malignant bone tumors such as localized and metastasized bone tumors, in particular osteosarcoma and Ewing's sarcoma. A preferred parvovirus includes a replication competent parvovirus H-1PV.

3 Claims, 11 Drawing Sheets

ONCOLYTIC VIROTHERAPY FOR THE THERAPY OF EWING'S SARCOMA

RELATED APPLICATIONS AND INCORPORATION BY REFERENCE

This application is a continuation-in-part application of international patent application Serial No. PCT/EP2012/002539 filed Jun. 15, 2012, which published as PCT Publication No. WO 2012/171654 on Dec. 20, 2012, which claims benefit of European patent application Serial No. EP11004884 filed Jun. 15, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention provides a parvovirus, preferably H-1PV, for the treatment of mesenchymal tumors, preferably malignant bone tumors such as localized and metastasized bone tumors, in particular osteosarcoma and Ewing's sarcoma.

BACKGROUND OF THE INVENTION

Sarcoma is a cancer of the soft tissue (muscle, fat, nerve, or connective tissue) or bone. Sarcomas encompass a group of over 40 different types of tumors. In general, sarcomas are considered quite rare, accounting for less than 1% of all adult cancer diagnoses, with approximately 10,000 new cases annually in the soft tissues and 2,400 new cases annually in the bone. Sarcomas are considered mesenchymal cancer arising either primarily from bone cancers (different from bone metastases from other cancers), or from soft tissues such as muscle (rhabdomyosarcoma), fat tissue (liposarcoma) or smooth muscle cells (leiomyosarcoma). They are named based on the tissue from which they arise. For example, chondrosarcomas arise from cartilage, osteosarcomas arise from bone, and fibrosarcomas arise from fibrogenic tissue.

Osteosarcoma is the most common type of bone sarcoma, accounting for approximately 35% of bone tumors. Chondrosarcoma is the second most common type in adults (accounting for 30% of bone sarcomas), and Ewing's sarcoma is the second most common type in children. All other types are extremely rare, each accounting for less than 1% of all bone sarcomas. Within these types, there are further histological subtypes—for example, there are seven different types of osteosarcomas (see, www.cancer.gov/cancertopics/pdq/treatment/osteosarcoma/HealthProfessional/page4).

Oncolytic viruses are viruses selectively or preferentially infecting and killing transformed cells while sparing normal tissues. In addition to the oncolytic effect observed both in vitro and in vivo, these viruses also provide immune-stimulatory signals inducing the elimination of virus-infected tumor cells. Thereby the innate and adaptive immune systems gain access to tumor antigens, which results in cross-priming and vaccination effects.

A systematic preclinical evaluation of oncolytic virotherapy approaches for osteosarcoma treatment had been performed using the two wild type viruses Semliki Forest virus (SFV), (1), and Seneca Valley Virus (SVV, NTX-010®), (2). In a pre-clinical pediatric screening approach six osteosarcoma xenograft SCID mouse models only low treatment response was observed for the intravenous treatment with Seneca Valley Virus (SVV i.e. NTX-10®). Only one out of six xenograft models showed significantly extended event-free survival (EFS) in the treated mice—whereas data on OS were not shown (2). The second wild type virus, SFV, was shown to significantly increase survival in both a subcutaneous and a second ortho-topic osteosarcoma xenograft model in nude mice (1). Additionally two recombinant adenoviruses re-targeted to osteosarcoma were tested (3, 4). Intratumoral injections of Ad5-Delta24RGD into established human osteosarcoma xenografts refractory to chemotherapeutic treatment caused a significant tumor-growth delay (5). Another conditionally replicating adenovirus based on Ad5Delta24, Ad-OC-E1a, expresses the viral E1A gene under the control of the promoter of the bone matrix protein osteocalcin which targets Ad-OC-E1a replication to cells of the bone matrix and malignant cells derived thereof. Intravenous application of Ad-OC-E1a significantly reduced the size of pulmonary metastatic osteosarcoma nodules in a xenograft mouse model (6).

Ewing's sarcoma can occur in the bone or soft tissue (called extra-osseous), and this is important when treatment options are considered. The large majority of cases occur in the bones, and the diagnosis is most common in the teenage years. PNET (primitive neuroectodermal tumor) is a type of sarcoma closely related to Ewing's. PNET can occur in the bone or the central nervous system. PNET of the bone is treated the same as Ewing's sarcoma, but PNET in the brain or spinal cord is a genetically different tumor that is treated differently. Ewing's, PNET, Askin's tumors and neuroepithelioma all contain the same genetic abnormality, called an 11-22 chromosomal translocation (t11;22). Because of this similarity, these tumors are referred to as the Ewing's sarcoma family of tumors and are treated similarly.

Few therapeutic attempts based on oncolytic viruses have been reported for Ewing's sarcoma so far. The genetically engineered oncolytic HSVs NV1020 and G207 had also been tested on a panel of ten sarcoma cell lines. However, compared to RMS and osteosarcoma cell lines Ewing's sarcoma cell lines showed the lowest susceptibility to oncolytic HSVs in vitro (7). The susceptibility of Ewing's sarcoma cell lines to adenovirus-mediated transduction could also be demonstrated, since the expression of adenovirus-receptor and Coxsackie-adenovirus-receptor was observed on these cell lines. Moreover, a recombinant conditionally replicating adenovirus induced significant oncolytic effects on Ewing's sarcoma cell lines in vitro (8). In animal models only two oncolytic viruses were tested: the wild type virus SVV and a recombinant AAV expressing an anti-angiogenic soluble VEGF-ligand. Both viruses could not be shown to be therapeutically effective. A preventive intravenous application of a rAAV expressing an anti-angiogenic soluble VEGF-ligand into the portal vein of SCID mice prevented the subsequent engraftment of Ewing's sarcoma xenografts (10). In four Ewing's sarcoma xenograft models the systematic preclinical evaluation of SVV did not induce any significant therapeutic effects (2). So far no application of rodent parvoviruses to Ewing's sarcoma has been described.

Typically, current treatment of bone sarcoma is multimodal and risk-adapted according to the therapy study EURAMOS1 (for osteosarcoma) of the GPOH including neo-adjuvant polychemo-therapy, tumor resection and radiotherapy. According to EWING 2008 high risk (R2 and R3) Ewing's sarcoma patients receive high dose chemotherapy in combination with the transplantation of autologous stem cells. In principle, radiation and intravenous drips of cytotoxic chemicals are used in combination. The side effects, both short term and long term, can be harsh. Short term negative side effects of chemotherapy include loss of hair and eyebrows, loss of appetite, having food taste peculiar, mouth sores, nausea, vomiting, loose stools or constipation (due to less food intake), fatigue, mental fogginess and inability to resist infections. Another short term disadvantage is that treatment is time-consuming. Long term side effects (depending on the type of cancer) include infertility, heart problems, damage to the central nervous system or damage to vital organs such as the lungs or liver.

Citation or identification of any document in this application is not an admission that such document is available as prior art to the present invention.

SUMMARY OF THE INVENTION

Therefore, it is the object of the present invention to provide means for the efficient treatment of mesenchymal tumors, preferably osteosarcoma and Ewing's sarcoma which overcomes the disadvantages of the current therapies, i.e., is efficient and shows less side effects compared to current therapy modalities.

The present invention is based on the applicant's findings of the induction of oncolysis in osteosarcoma and Ewing's sarcoma cell lines after application of H-1PV, an oncolytic non-pathogenic replication competent parvovirus.

In summary, the experiments resulting in the present invention show that H-1PV infection of mesenchymal malignant cells, e.g., osteosarcoma or Ewing's sarcoma cells, represents a new and highly effective therapy with only very low side effects.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Osteosarcoma and Ewing's sarcoma cells are susceptible to H-1PV infection. Infection of human osteosarcoma (U2-OS, SaOS-2, MG-63) and Ewing's sarcoma (SK-ES-1, RD-ES) cells with GFP expressing recombinant, replication-deficient, H-1 virus (H-1EGFP) at various MOIs (0, 1, 10, 50 pfu/cell). Besides osteosarcoma and Ewing's sarcoma cell lines, a neuroblastoma cell line (WAC-2), serving as positive control, and human non-transformed osteoblast and fibroblast cells were infected.
 (a) Phase contrast (upper rows) and fluorescent (rows below) microscopy pictures taken two days after infecting cells with H1-EGFP. Magnification: 1:20,000.
 (b) Graphs representing the number of GFP expressing cells at various MOIs (0, 1, 10, 50 pfu/cell) at different time-points after infection. GFP expressing cells were counted under the fluorescent microscope in a pool of 4,000 cells seeded; for the experiments with non-transformed osteoblasts and fibroblasts, $10_4$ cells were seeded.

FIG. 2: Parvoviral proteins are expressed in osteosarcoma and Ewing's sarcoma cells. Western blot results using viral capsid protein 1 and 2 (VP1 and VP2) specific antibody. Cells were seeded and after 12 hours infected with H-1PV an MOI of 1 pfu/cell or mock-infected with an equal dilution of iodixanol. Samples for Western blot analysis were collected every 24 hours. VP1 and VP2 specific bands appear in cellular lysates of H-1PV infected osteo-sarcoma and Ewing's sarcoma cells.

FIG. 4: Cytomorphological changes in infected osteosarcoma and Ewing's sarcoma cells indicate a cytopathic effect of H-1PV. Pictures of cells were taken before performing the cytotoxicity tests, at day 3 and 6 for bone tumor cells and positive control and at day 7 for non-transformed fibroblast and osteoblast cells. Used magnification scale for U-2 OS, SK-ES-1, WAC-2, fibroblast and osteoblast cells is 1:104, whereas for SaOS-2, MG-63, and RD-ES is 1:204. In case of bone tumor cells for day 3 determinations 1000 cells/well were seeded, whereas for day 6 determinations 500 cells/well were seeded in 96 well plates. For WAC-2 200 cells/well were seeded both for day 3 and day 6 determinations in 96 well plates. 2,500 non-transformed osteoblast and fibroblast cells/well were seeded in the same 96 well plates.

Therefore, after 12 hours after seeding them cells were infected with wt H-1PV at indicated MOIs and allowed to grow until mock infected control cells became confluent. Three and six days after infection, metabolic activity thus cellular viability was determined using MTT-tests. Values for metabolic activity are expressed relative to mock-treated control cells. LDH-release assays (right panel): Cytotoxicity of H-1PV on osteosarcoma and Ewing's sarcoma cell lines was quantified by LDH-release assays. For this, 50 μl of the supernatant of the cells seeded for MTT-tests was taken and LDH-release was assayed after H-1PV infection (as with MTT-tests) to measure cytolysis. LDH activity in supernatants was expressed relative to cells completely lysed by triton lysis. Means from 8 experiments and respective double standard errors are shown both for MTT-tests and LDH-release assays.

DETAILED DESCRIPTION OF THE INVENTION

The present invention provides a parvovirus for use in a method for the treatment of a mesenchymal tumor, preferably a bone tumor.

Some autonomous parvoviruses belong to the category of so called oncolytic viruses. Parvoviruses are small (25-30 nm) non-enveloped particles containing a 5.1 kb single-stranded DNA genome, from which the two non-structural proteins (NS1, NS2) and the two capsid (VP1, VP2) proteins are expressed.

Parvovirus H-1PV has the unique advantage of triggering a distinct death process, namely the cytosolic relocation and activation of lysosomal proteases (cathepsins). Several members of the parvovirus genus (H-1PV, MVM, LuIII), whose natural hosts are rodents, are presently under consideration for cancer gene therapy applications due to their failure to transform host cells, capacity for asymptomatic infection of humans, and ability to preferentially propagate in (oncotropism) and kill (oncolysis) neoplastically transformed cells. MVMp and H-1PV viruses have been shown to exert onco-suppressive activities in vivo, i.e. they are able to inhibit the formation of spontaneous, chemically or virally induced tumors in laboratory animals. Vectors based on a parvoviral expression cassette retain the oncotropic features of the wild type viruses.

The oncolytic effects of H-1PV have been studied in vitro and in vivo on a variety of human entities such as lymphoma, pancreatic cancer, glioblastoma cell lines, hepatoma, breast cancer (10) and neuroblastoma (11). However, the oncolytic effect of H-1PV on pediatric bone tumors had not been studied so far. In the studies resulting in the present invention a pre-clinical in vitro assessment of the application of oncolytic H-1PV for the treatment of pediatric osteosarcoma and Ewing's sarcoma cell lines was performed. Infection efficiency, viral replication, and lytic activity of H-1PV were analyzed in detail in three osteosarcoma and two Ewing's sarcoma cell lines with different p53 mutation status.

Oncoselectivity of the virus was confirmed by the infection of short term cultures of non-malignant infant cells of mesenchymal origin. Human neonate foreskin fibroblasts and human osteoblasts in short term culture did not reveal any significant effect of H-1PV on viability or morphology of the cells below virus doses of 50 plaque forming units [pfu] per cell. All bone tumor cell lines could be infected by H-1PV as shown by infection with H-1EGFP, a recombinant, EGFP-expressing replication-deficient virus. With wild type H-1PV lytic infection was induced in four out of five osteosarcoma cell lines (Sa-OS, CAL-72, U2-OS, and H-OS) and all Ewing's sarcoma cell lines (MHH-ES-1, TC-71, RD-ES, SK-ES-1 and CADO-ES) examined. Three out of five osteosarcoma cell lines and four out of five Ewing's sarcoma cell lines showed 50% response to treatment at MOIs between below 1 and 5 p.f.u. per cell. Active replication of H-1PV could be exemplarily demonstrated in one Ewing's sarcoma cell line with an increase of virus titers up to 10-fold within 96 hours after infection. The lytic effect of H-1PV in sarcoma cell lines was observed independent from their p53 mutation status.

Infection efficiency, rapid virus replication and relevant lytic effects on Ewing's sarcoma and most osteosarcoma cells together with the low toxicity of H-1PV for non-transformed mesenchymal cells, render this parvovirus a promising candidate for oncolytic virotherapy of malignant diseases of the skeletal system.

The term "parvovirus" as used herein may comprise wild-type viruses, replicating viruses and modified replication-competent derivatives thereof and non-replicating viruses, CPG-armed viruses as well as related viruses or vectors based on such viruses or derivatives. Suitable parvoviruses, derivatives, etc. which are useful for therapy, are readily determinable within the skill of the art based on the disclosure herein, without undue empirical effort. Replication competent viruses are preferred for the use of the present invention. Treatment is achieved by killing of the cancer cells, i.e., the cancer cells are killed by the oncolytic and cytotoxic activity of the parvovirus such that these cells are no longer capable of generating tumors.

Preferably, said parvovirus is formulated as a pharmaceutical composition, wherein the parvovirus is present in an effective dose and combined with a pharmaceutically acceptable carrier. "Pharmaceutically acceptable" is meant to encompass any carrier which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Additional pharmaceutically compatible carriers can include gels, bioadsorbable matrix materials, implantation elements containing the parvovirus (therapeutic agent), or any other suitable vehicle, delivery or dispensing means or material(s). Such carriers can be formulated by conventional methods and can be administered to the subject at an effective dose.

An "effective dose" refers to amounts of the active ingredients that are sufficient to effect treatment of the sarcoma. An "effective dose" may be determined using methods known to one skilled in the art (see for example, Fingl et al., The Pharmacological Basis of Therapeutics, Goodman and Gilman, eds. Macmillan Publishing Co., New York, pp. 1-46 ((1975)).

Administration of the parvovirus may be effected by different ways, e.g. by intravenous, intratumoral, intraperitoneal, subcutaneous, intramuscular, topical or intradermal administration. The route of administration, of course, depends on the kind of therapy. Preferred routes of administration are intravenous (i.v.), intratumoral or endobronchial administration. Endobronchial virus application may be used for the treatment of pulmonary metastases frequently occurring as the first systemic relapse in osteosarcoma and particularly in Ewing's sarcoma patients. If infectious virus particles are used which have the capacity to penetrate through the blood-brain barrier, treatment could be performed or at least initiated by intravenous injection of, e.g., H1 virus. However, long term intravenous treatment could become inefficient by the formation of neutralizing antibodies to H1 virus. Therefore, different modes of intratumoral virus application might be preferable. The parvovirus or derived vectors can also be injected into the hepatic or pulmonary metastases of bone tumors. This could be achieved via ultrasound or CT-guided intrahepatic punctions or bronchioscopy-assisted delivery of the virus into the metastatic pulmonary nodules. Combinations of the above mentioned methods of application are also possible.

The dosage regimen of the parvovirus is readily determinable within the skill of the art, by the attending physician based on patient data, observations and other clinical factors, including for example the patient's size, body surface area, age, sex, the particular parvovirus etc. to be administered, the time and route of administration, the type of mesenchymal tumor, general health of the patient, and other drug therapies to which the patient is being subjected.

As another specific administration technique, the parvovirus can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus to be injected locally at various times without further surgical intervention. The parvovirus can also be injected into the tumor by stereotactic surgical techniques or by neuronavigation targeting techniques.

Administration of the parvovirus can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvovirus is from an implanted device constructed and arranged to dispense the parvovirus to the desired tumor. For example, wafers can be employed that have been impregnated with the parvovirus, e.g., parvovirus H1, wherein the wafer is attached to the edges of the resection cavity at the conclusion of surgical tumor removal. Multiple wafers can be employed in such therapeutic intervention. Cells that actively produce the parvovirus, e.g., parvovirus H1, can be injected into the bone tumor, or into the tumor cavity after tumor removal.

The therapy according to the invention is useful for the treatment of mesenchymal tumors, i.e., a localized or metastasized bone tumor, in particular osteosarcoma or Ewing's sarcoma and can significantly improve the prognosis of said diseases. The increased anti-tumor response by infection with oncolytic parvoviruses combines the direct and specific cytotoxicity of this virus against tumor cells (but not healthy cells) with a secondary and long term anti-tumor activity. In case of relapse, Ewing's sarcoma cannot be treated with curative intent. Therefore, alternative therapeutic options, such as oncolytic parvovirotherapy, which is able to kill Ewing's sarcoma cell in vitro at doses of input virus comparable to the doses required for adult high-grade glioma cell lines promise relevant therapeutic efficacy.

In a preferred embodiment of the present invention, the cells of the mesenchymal tumor to be treated are (a) resistant to chemotherapy or radiotherapy, or (b) potentially relapsing tumor cells.

In a further preferred embodiment of the present invention, the parvovirus is a rodent parvovirus, particularly preferred is parvovirus H1 (H1PV) or a related parvovirus such as LuIII, Mouse minute virus (MMV), Mouse parvovirus (MPV), Rat minute virus (RMV), Rat parvovirus (RPV) or Rat virus (RV).

Patients treatable by the parvovirus according to the invention include humans as well as non-human animals. Examples of the latter include, without limitation, animals such as cows, sheep, pigs, horses, dogs, and cats.

Treatment using a parvovirus can be combined with further kinds of therapy, e.g., chemotherapy using, e.g., a chemotherapeutic agent like etoposide, ifosfamide, adriamycin, vincristin, doxicyclin.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Materials and Methods (A) Cell Culture

The human osteosarcoma cell lines H-OS, CAL-72, U2-OS, SaOS-2, and MG-63 and the Ewing's sarcoma cell lines MHH-ES, TC-71, SK-ES-1, RD-ES and CADO-ES were obtained from CLS (Cell Lines Service, Eppelheim, Germany). The five osteosarcoma cell lines (H-OS, SaOS-2, CAL-72, U2-OS and MG-63) were grown under standard conditions 37° C., 5% $CO_2$ in Dulbecco's Modified Eagles Medium (Sigma Aldrich, Munich, Germany), supplemented with 10% heat-inactivated fetal bovine serum, and 1% penicillin-streptomycin. Ewing's sarcoma cell lines (MHH-ES, TC-71, MHH-ES, SK-ES-1 and RD-ES) were grown in RPMI1640 cell culture medium, supplemented with 10% heat-inactivated FBS, and 1% penicillin-streptomycin.

(B) Virus Production and Infection

Wild-type H-1PV was produced by infecting NBK-324K human embryonic kidney cells, and purified by filtration (maximal diameter of particles 0.2 μm) and iodixanol gradient centrifugation. The contamination of virus stocks with endotoxins was <2.5 EU/ml. Cells were infected with H-1PV as adhesively growing cultures 12 to 24 h after cell counting and seeding.

(C) Detection of Infectious H-1PV Particles

Virus titres were determined as described previously (12). NB-324K cells ($7.6 \times 10_3$ cells/well) were seeded in 96-well plates 24 h prior to the assay. Cells were infected by 10-fold serial dilutions of the supernatant of the previously infected osteosarcoma or Ewing's sarcoma cell lines and incubated for 72 h at 37° C., 5% $CO_2$. After alkaline lysis (0.75 M NaOH), DNA was transferred to a nylon membrane, cross-linked, and hybridized with a NS-1 specific probe radiolabeled with $P_{32}$. Blots were exposed to X-ray film for autoradiography. Titration experiments were always performed in triplicates. The virus was applied at multiplicities of infection (MOI, expressed in plaque-forming units per cell; pfu) as indicated.

(D) Viral DNA Extraction and Quantitative Real-Time PCR

The supernatant of the infected cell cultures was collected at different time points after infection. The supernatants were treated with 50 U per ml Benzonase Nuclease (Ultrapure grade; Sigma), at 37° C. for 30 min to digest remaining genomic DNA. To release viral DNA from virions, 10 μl of cell extract were subjected to alkaline lysis in 1 M NaOH in TE buffer at 56° C. for 30 min. Lysis was stopped by adding 960 μl of 40 mM HCl. After neutralization with an equimolar concentration of HCl the samples were diluted 1:100 with sterile water and directly analyzed.

The supernatant was incubated in TE buffer for 30 min at 56° C. Quantification of viral DNA was carried out by real-time qPCR amplification of 141 nt DNA fragment within the NS1 gene using the following primers NS1-FOR: 5'-GCG CGG CAG AAT TCA AAC T-3' (SEQ ID NO: 1), NS1-REV: 5'-CCA CCT GGT TGA GCC ATC AT-3' (SEQ ID NO: 2).

The amplicon was detected using the NS1-specific TaqMan™ probe 5'-6-FAM-ATGCAGCCAG-ACAGTTA-Q-MGB 3' (SEQ ID NO: 3) (Applied Biosystems by Life Technologies, Carlsbad (Calif.), USA) in an ABI Prism 7700 thermal cycler Applied Biosystems by Life Technologies, Carlsbad (Calif.), USA) and analyzed by means of SDS 2.1 software (Applied Biosystems by Life Technologies, Carlsbad (Calif.), (USA) as described elsewhere (13). A plasmid that contained the NS1-sequence in serial dilutions in the range of 101-108 copies/reaction was used to standardize the qPCR. Individual reaction mixtures (20 µl) consisted of 1× TaqMan Universal PCR Master Mix™ (Applied Biosystems), 0.3 µM labelled NS1-TaqMan™ probe, 0.3 µM of each primer and 3 µl template. PCR conditions were 2 minutes at 50° C. (destruction of contaminating template by AmpErase™), then 10 minutes 95° C., followed by 40 cycles of denaturation at 95° C. for 15 seconds and annealing/extension at 60° C. for 60 s.

(E) Microscopy

Phase contrast images were generated using an inverted phase contrast microscope (Olympus; Model CKX41) and Cell B software for image processing (Olympus Europa GmbH, Hamburg, Germany). Other phase contrast images were obtained using a Leica DFC350 FX™ camera (Leica Microsystems Biosystems, Wetzlar, Germany) and the Leica FireCam™ software for Macintosh.

(F) Assessment of Cell Viability and Lysis

Metabolic activity of the cells was determined based on the 3-(4,5-dimethylthiazol-2-yl)-2,5-diphenyltetrazolium bromide (MTT) assay as recommended by the manufacturer (Sigma-Aldrich, St. Louis, Mo., USA). Cells (between 1,000 and 2,000 cells per well) were cultured in 96-well plates and infected at MOIs indicated in the Figures. After 3 and 6 days, cells were washed in PBS and incubated with 0.5 µg/ml MTT-solution for up to 2 hours. After discarding the supernatant and drying the cells, 100 µl isopropanol per well were added. Extinction values were photometrically determined at 570 nm (Multiscan Plus™, Titertek Instruments Inc., Huntsville, Ala., USA).

Cell lysis was determined by measuring the release of lactate dehydrogenase into culture medium by use of the Cytotox 96 cytotoxicity assay Kit™ (Promega Biosystems Promega Corporation, Madison Wis., U.S.A.) as recommended by the manufacturer.

Example 2

Osteosarcoma and Ewing's Sarcoma Cells are Susceptible to H-1PV Infection

Figure 1A:
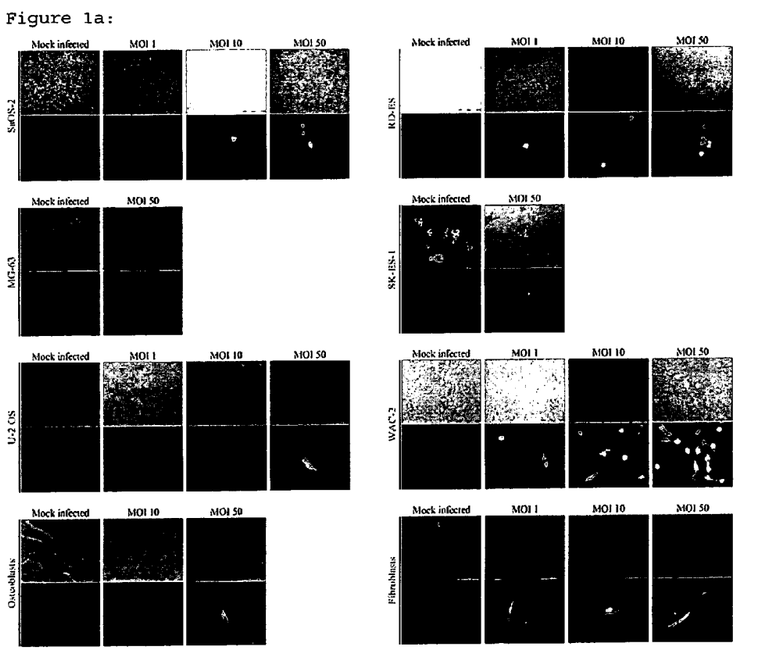
Figure 1B:
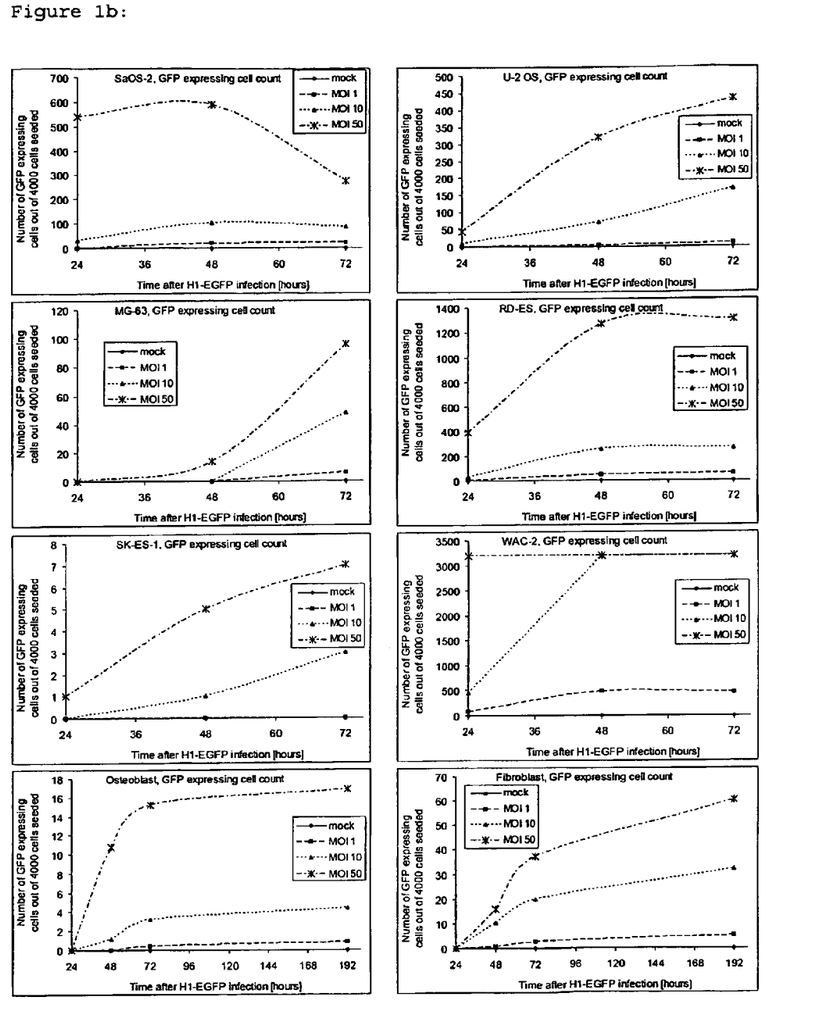

To determine if H-1PV was able to infect osteosarcoma and Ewing's sarcoma cells, cells were exposed in parallel to one and 50 replication units per cell of recombinant, replication-deficient H-1 virus (H-1EGFP) virus expressing GFP. WAC-2 neuroblastoma cells (kindly provided by Prof. O. Witt, CCU Pediatric Oncology, DKFZ, Heidelberg) served as a positive control. EGFP expression could be detected in all cell lines with H-1EGFP, indicating successful infection gene expression driven by the viral promoter in non-transformed mesenchymal cells and in bone cancer cells (FIGS. 1a and b).

Example 3

H-1PV Proteins are Expressed in Osteosarcoma and Ewing's Sarcoma Cells

Figure 2:
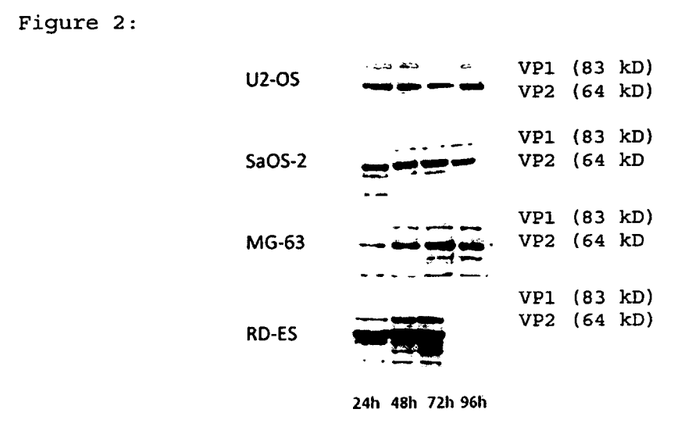

In order to demonstrate that the proteins of wtH-1PV were expressed in infected osteosarcoma and Ewing's sarcoma cells, Western blot analysis of VP1 and VP2 capsid proteins in infected cells was performed. NS1 and NS2 are non-structural proteins required for infection of host cells (14), and VP1/2 are structural viral capsid proteins (15). Subsequent to infection with one pfu wild type H-1PV per cell, the viral capsid proteins were expressed in all bone cancer cell lines investigated during 96 h after infection (FIG. 2).

Example 4

H-1PV Actively Replicates in Osteosarcoma and Ewing's Sarcoma Cells

Figure 3A:
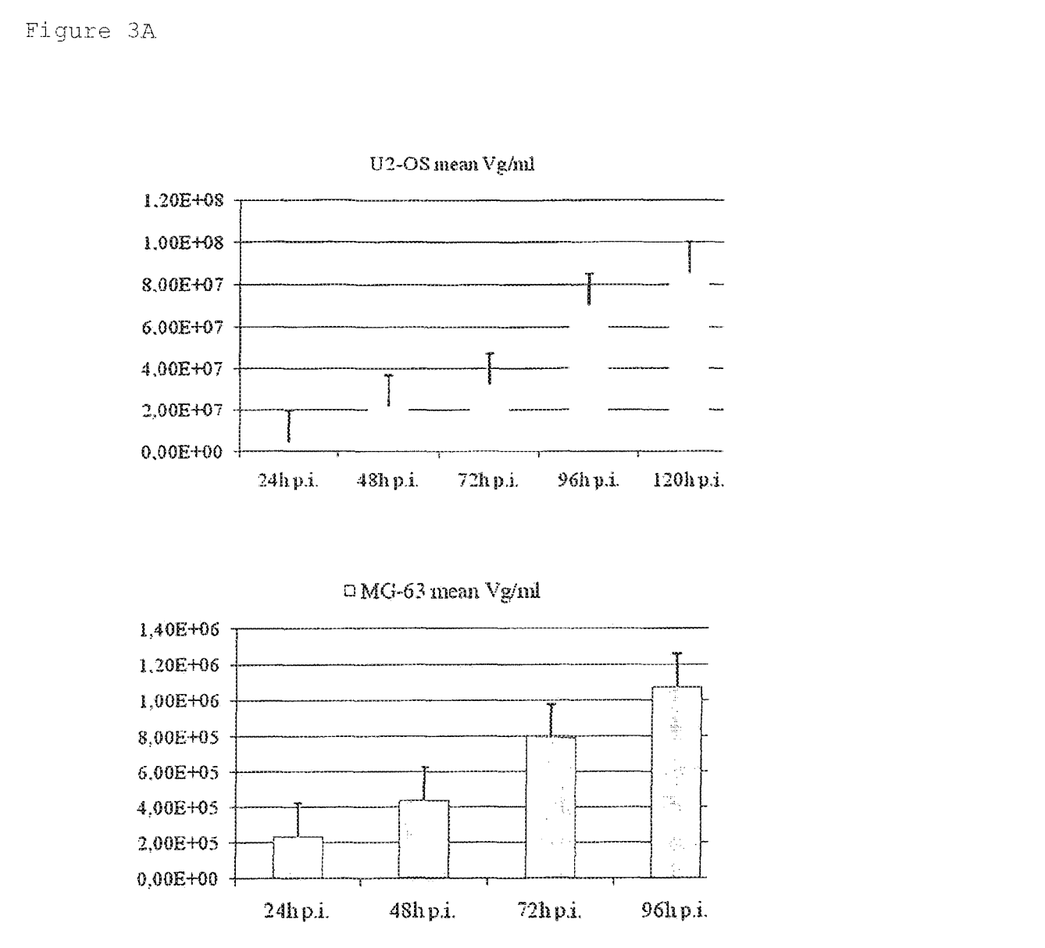
FIGS. 3A-3B: H-1PV actively replicates in osteosarcoma and Ewing's sarcoma cells.
Figure 3B:
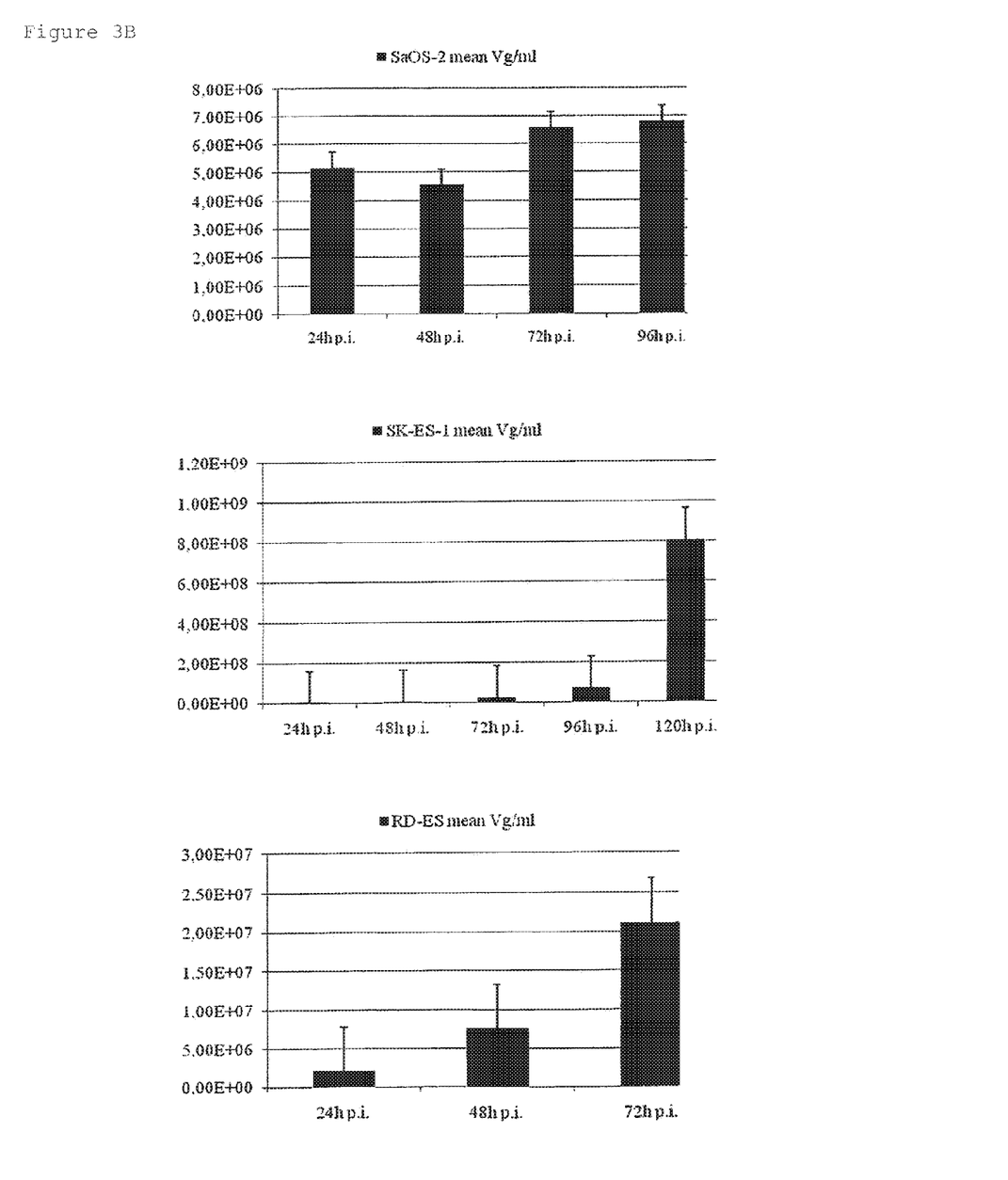

In order to address the question whether H-1PV was able to multiply in bone cancer cells, osteosarcoma and Ewing's sarcoma cells were infected with wild type H-1PV. The titers of viral genome copies in the supernatant of the infected cells were determined by real-time PCR in a time period ranging from 24 to 96 h after infection. In osteosarcoma cell lines no efficient viral replication could be observed. Only in the RD-ES Ewing's sarcoma cell line efficient virus replication could be demonstrated (FIG. 3), which is comparable to the replication efficiency in human high-grade glioma cell lines (16).

In order to confirm the multiplication of infectious progeny H-1PV, infectious particle assays with supernatants of the same infected bone cancer cell lines in culture were performed. The progeny H-1 viruses were biologically active, i.e. able to infect NBK-324K cells. Taken together, H-1PV could be proven to productively infect osteosarcoma and Ewing's sarcoma cells. Infection of these cells could be demonstrated to induce the expression of essential viral proteins. However, efficient viral replication and production of infectious H-1PV progeny could only be demonstrated in one out of two Ewing's sarcoma cell lines.

Example 5

H-1PV Induces Lytic Infection in Osteosarcoma and Ewing's Sarcoma Cell Lines

Figure 4:
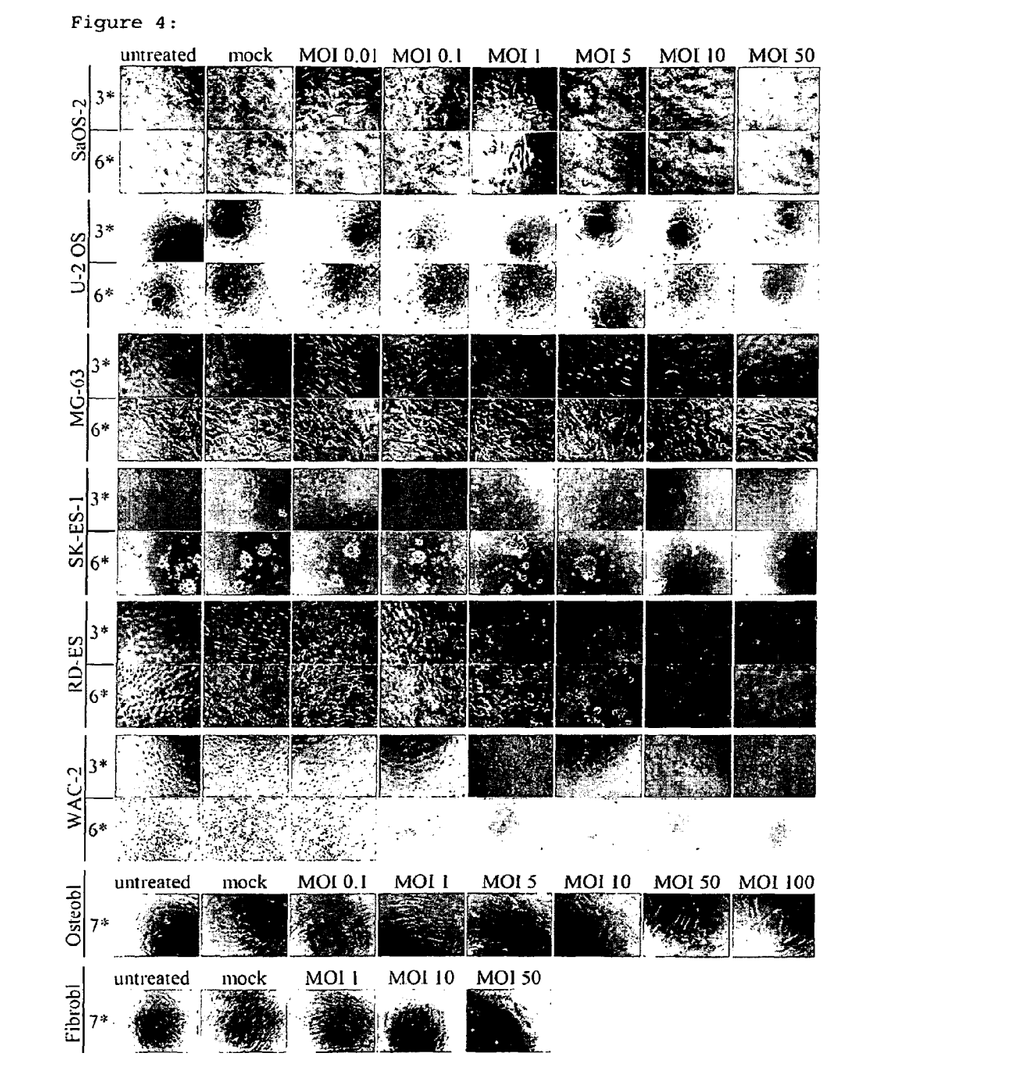
Figure 5A:
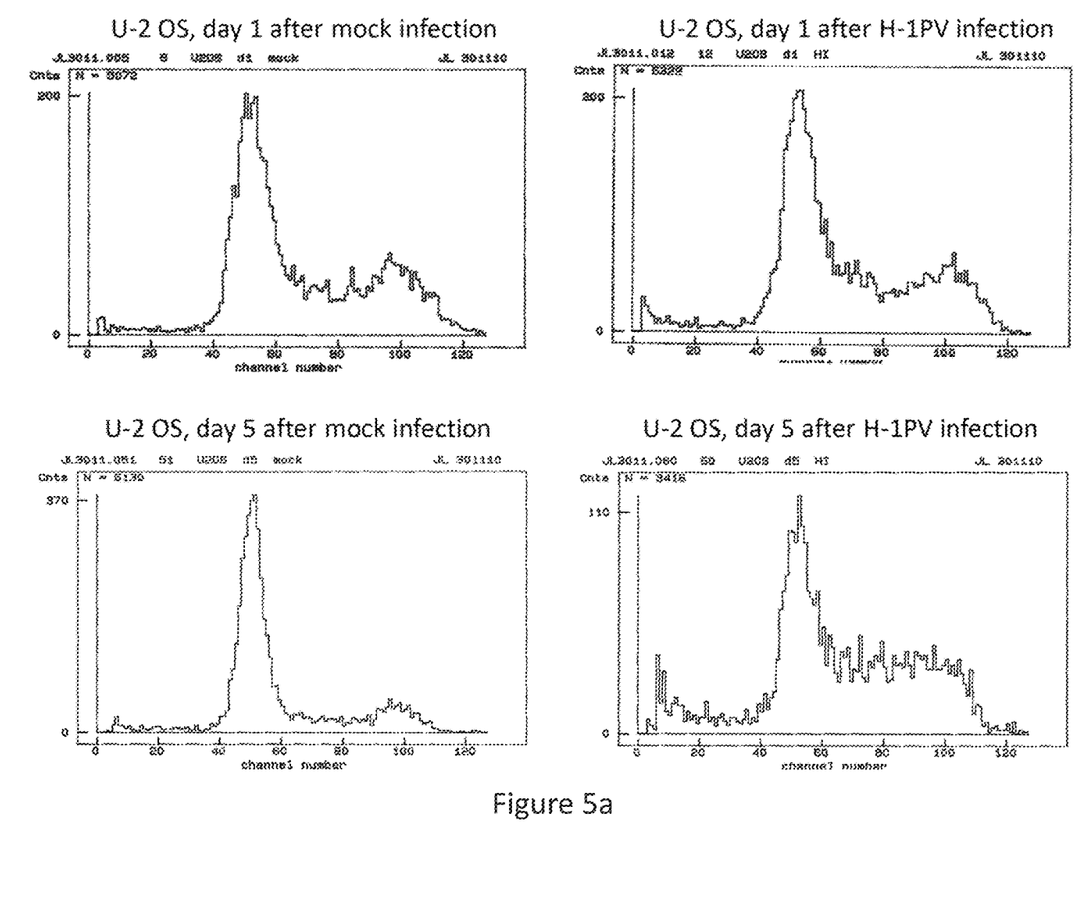
FIG. 5: Cell cycle analysis of H-1PV and mock infected osteosarcoma cells. H-1PV infection induced apoptosis in osteosarcoma cell lines. After infection with MOI 1 and subsequent propidium iodine staining cell cycle analysis was performed by flow cytometry. H-1PV infection was able to induce G2-arrest and the appearance of a sub-G1 population, as exemplarily shown for SaOS and U2-OS osteosarcoma cell lines.
Figure 5B:
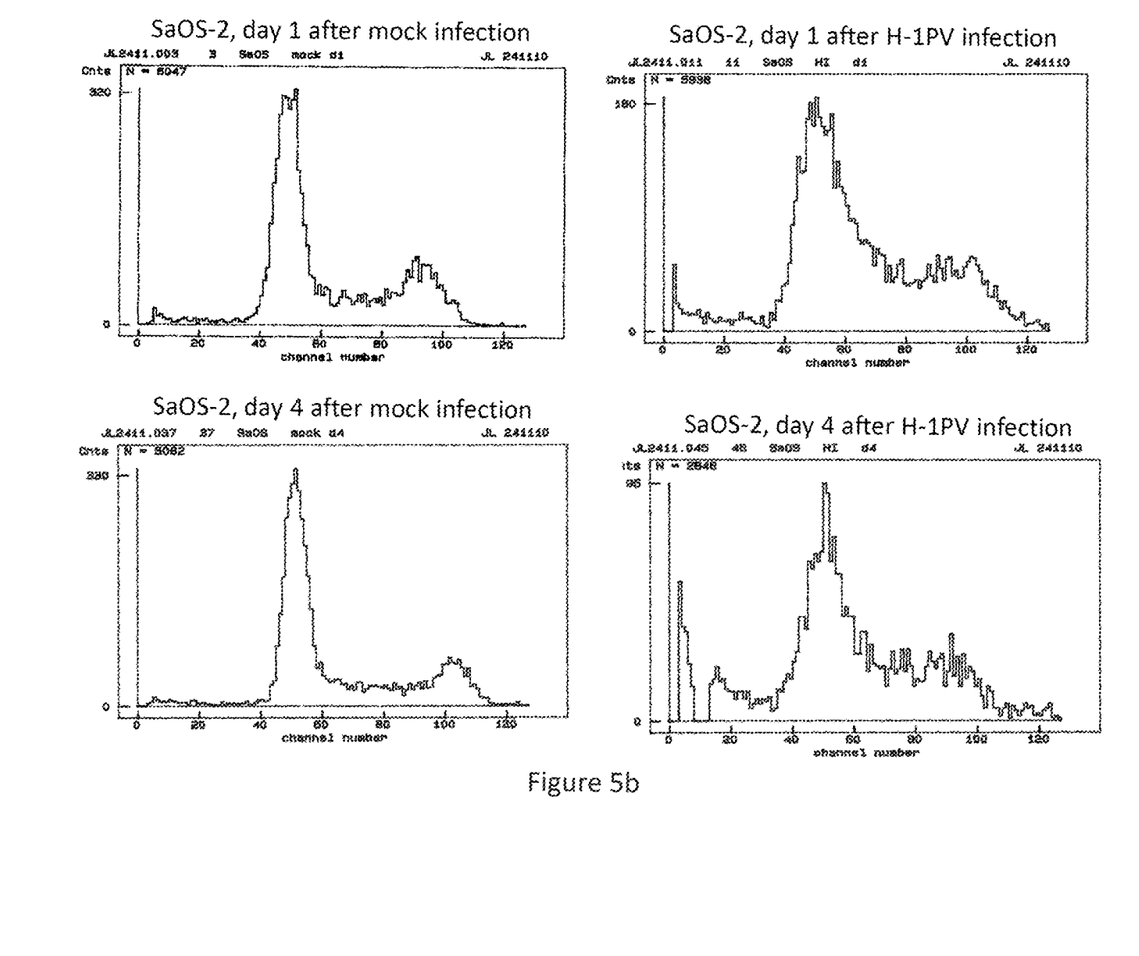

In order to test to what extent infection of osteosarcoma cells with wild type H-1 PV was lytic, the cytomorphology of the infected cells was documented by phase contrast microscopy. Three days after infection H-1PV could be shown to induce significant cytopathic effects on two out of three osteosarcoma cells applying an MOI of one to five pfu per cell or more (FIGS. 4 and 5). Three days after infection H-1PV could be shown to induce significant cytopathic effects on the two Ewing's sarcoma cell lines applying an MOI of one pfu per cell or more (FIGS. 4 and 5).

Example 6

Figure 6A:
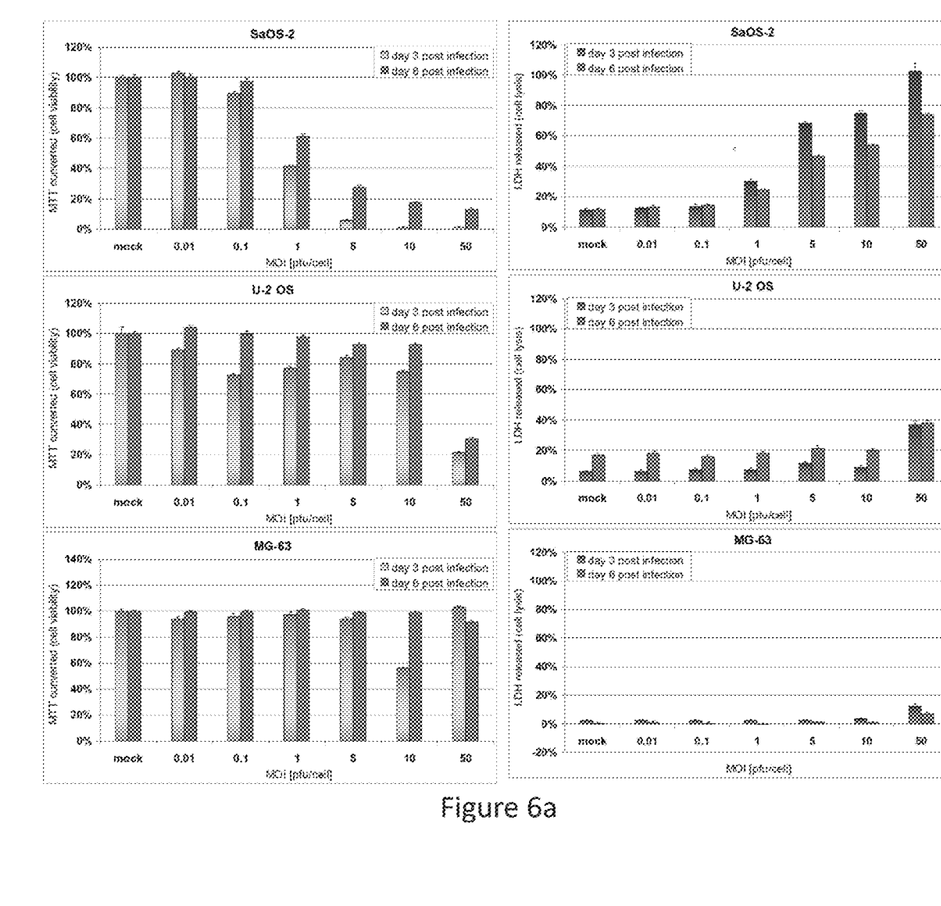
FIG. 6: H-1PV induces cytostatic effects on two out of three osteosarcoma cell lines and on two Ewing's sarcoma cell lines in a dose-dependent manner. MTT-test (left panel): To quantify cell viability of osteosarcoma and Ewing's sarcoma cell lines after H-1PV infection, MTT-tests were used.
Figure 6B:
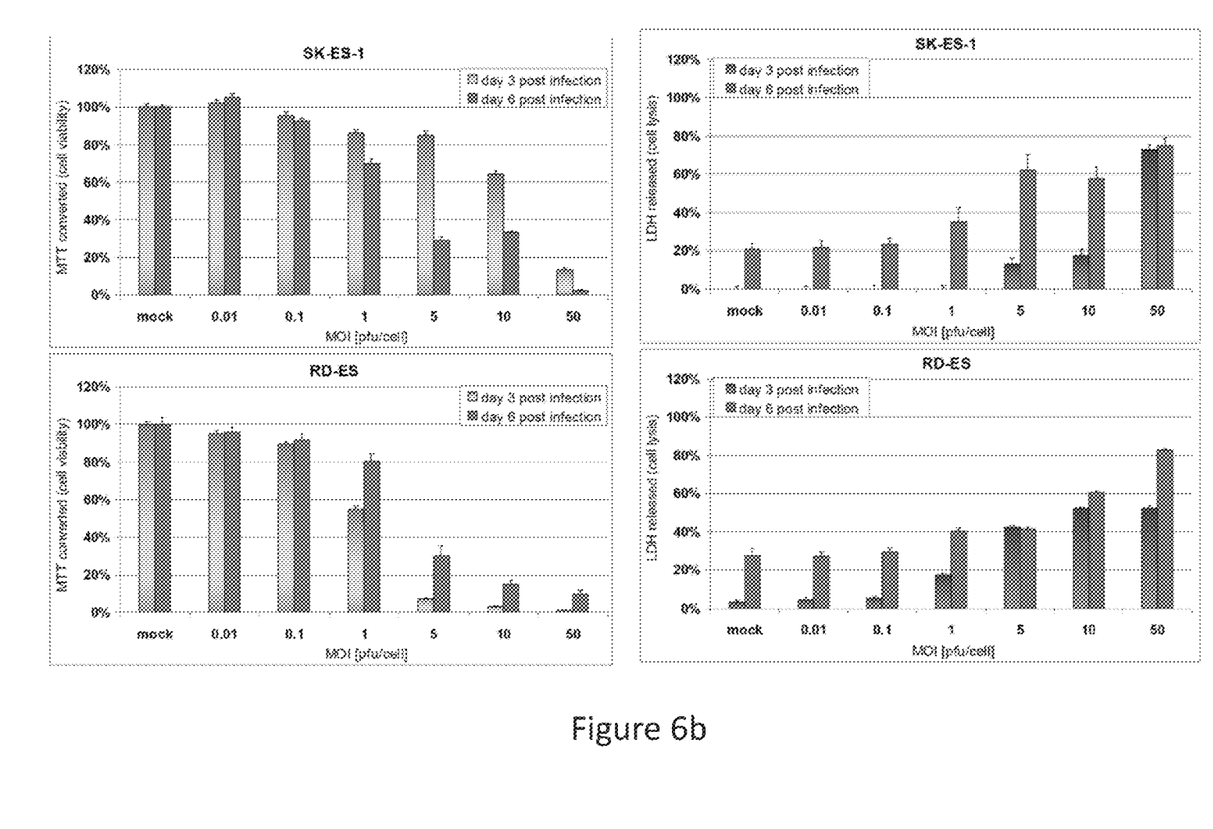
Figure 6C:
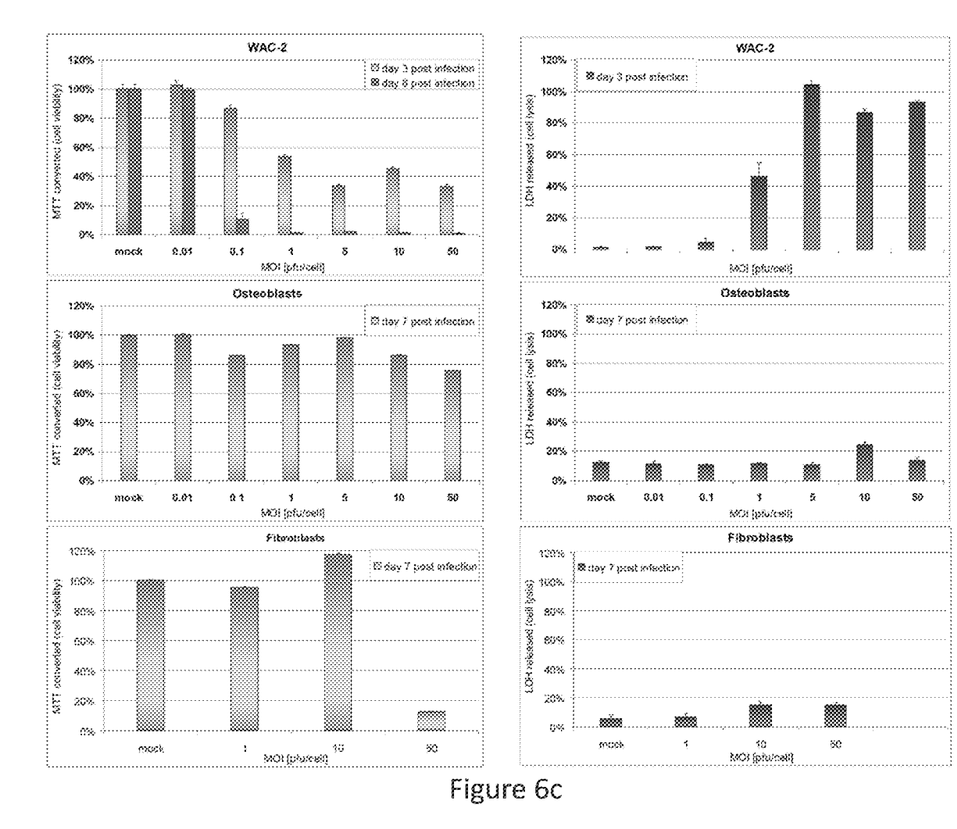

H-1PV Induces Cytostatic Effects on Two Out of Three Osteosarcoma Cell Lines and on Two Ewing's Sarcoma Cell Lines in a Dose-Dependent Manner The osteosarcoma cell lines H-OS, SaOS-2, U2-OS and MG-63 and the Ewing's sarcoma cell lines MHH-ES, RD-ES and SK-ES-1 were infected with increasing doses of wild type H-1PV between 0.01 and 10 pfu per cell. At days 3 and 6 after infection cell viability was determined by MTT test, and cellular lysis was analyzed by measurement of the extracellular LDH activity, released into the supernatant by lytic cells. Lysis of cells infected with the same MOI induced by application of a detergent served as reference for complete lysis (FIG. 5-6). Non-transformed fibroblasts and osteoblasts in short-term culture saved as negative controls. The results are also summarized in Table 1.

Example 7

Cytopathic Effects on Bone Cancer Cells Seem to be Mediated by Apoptosis

Osteosarcoma and Ewing's sarcoma cell lines were analyzed by propidium iodine staining and subsequent flow cytometry for the presence of a sub-G1 DNA content (less than 2n) cell population that is indicative of DNA fragmentation and apoptosis. H-1PV infection of osteosarcoma and Ewing's sarcoma was able to induce G2-arrest and the appearance of a sub-G1 population, as exemplarily shown for SaOS and U2-OS osteosarcoma cell lines (FIG. 6)

TABLE 1

TCID50 values for non-transformed and malignant bone cancer cells
The TCID50 values were determined based on the
investigation of cytopathic effects, metabolic
activity and cellular lysis of the infected cells.

| Cell line | LD50 [p.f.u./cell] | Tumor type |
|---|---|---|
| H-OS | <1 | osteosarcoma |
| CAL-72 | 1 | osteosarcoma |
| Sa-OS 2 | 5 | osteosarcoma |
| U-2 OS | 50 | osteosarcoma |
| MG-63 | >50 | osteosarcoma |
| MHH-ES-1 | <1 | Ewing's sarcoma |
| TC-71 | <1 | Ewing's sarcoma |
| RD-ES | 1 | Ewing's sarcoma |
| SK-ES-1 | 5 | Ewing's sarcoma |
| CADO-ES | 50 | Ewing's sarcoma |
| Osteoblasts | >50 | non-transformed |
| Fibroblasts (neonate) | >50 | non-transformed |

LIST OF REFERENCES (1) Ketola A, Hinkkanen A, Yongabi F, Furu P, Maatta A M, Liimatainen T, et al. Oncolytic Semliki forest virus vector as a novel candidate against unresectable osteosarcoma. Cancer Res 2008; 68:8342-50.
(2) Morton C L, Houghton P J, Kolb E A, Gorlick R, Reynolds C P, Kang M H, et al. Initial testing of the replication competent Seneca Valley virus (NTX-010) by the pediatric preclinical testing program. Pediatr Blood Cancer 2010; 55:295-303.
(3) Witlox M A, Lamfers M L, Wuisman P I, Curiel D T, Siegal G P. Evolving gene therapy approaches for osteosarcoma using viral vectors: review. Bone 2007; 40:797-812.
(4) Graat H C, van Beusechem V W, Schagen F H, Witlox M A, Kleinerman E S, Helder M N, et al. Intravenous administration of the conditionally replicative adenovirus Ad5-Delta24RGD induces regression of osteosarcoma lung metastases. Mol Cancer 2008; 7:9.
(5) Witlox A M, van Beusechem V W, Molenaar B, Bras H, Schaap G R, Alemany R, et al. Conditionally replicative adenovirus with tropism expanded towards integrins inhibits osteosarcoma tumor growth in vitro and in vivo. Clin Cancer Res 2004; 10:61-7.
(6) Li X, Jung C, Liu Y H, Bae K H, Zhang Y P, Zhang H J, et al. Anti-tumor efficacy of a transcriptional replication-competent adenovirus, Ad-OC-E1a, for osteosarcoma pulmonary metastasis. J Gene Med 2006; 8:679-89.
(7) Bharatan N S, Currier M A, Cripe T P. Differential susceptibility of pediatric sarcoma cells to oncolysis by conditionally replication-competent herpes simplex viruses. J Pediatr Hematol Oncol 2002; 24:447-53.
(8) Rice A M, Currier M A, Adams L C, Bharatan N S, Collins M H, Snyder J D, et al. Ewing sarcoma family of tumors express adenovirus receptors and are susceptible to adenovirus-mediated oncolysis. J Pediatr Hematol Oncol 2002; 24:527-33.
(9) Davidoff A M, Nathwani A C, Spurbeck W W, Ng C Y, Zhou J, Vanin E F. rAAV-mediated long-term liver-generated expression of an angiogenesis inhibitor can restrict renal tumor growth in mice. Cancer Res 2002; 62:3077-83.
(10) Rommelaere J, Geletneky K, Angelova A L, Daeffler L, Dinsart C, Kiprianova I, et al. Oncolytic parvoviruses as cancer therapeutics. Cytokine Growth Factor Rev 2010.
(11) Lacroix J, Leuchs B, Li J, Hristov G, Deubzer H E, Kulozik A E, et al. Parvovirus H1 selectively induces cytotoxic effects on human neuroblastoma cells. Int J Cancer 2010; 127:1230-9.
(12) Angelova A L, Aprahamian M, Grekova S P, Hajri A, Leuchs B, Giese N A, et al. Improvement of gemcitabine-based therapy of pancreatic carcinoma by means of oncolytic parvovirus H-1PV. Clin Cancer Res 2009; 15:511-9.
(13) Abschuetz A, Kehl T, Geibig R, Leuchs B, Rommelaere J, Regnier-Vigouroux A. Oncolytic murine autonomous parvovirus, a candidate vector for glioma gene therapy, is innocuous to normal and immunocompetent mouse glial cells. Cell Tissue Res 2006; 325:423-36.
(14) Caillet-Fauquet P, Perros M, Brandenburger A, Spegelaere P, Rommelaere J. Programmed killing of human cells by means of an inducible clone of parvoviral genes encoding non-structural proteins. EMBO J 1990; 9:2989-95.
(15) Chen Y Q, Tuynder M C, Cornelis J J, Boukamp P, Fusenig N E, Rommelaere J. Sensitization of human keratinocytes to killing by parvovirus H-1 takes place during their malignant transformation but does not require them to be tumorigenic. Carcinogenesis 1989; 10:163-7.
(16) Herrero Y C, Cornelis J J, Herold-Mende C, Rommelaere J, Schlchofer J R, Geletneky K. Parvovirus H-1 infection of human glioma cells leads to complete viral replication and efficient cell killing. Int J Cancer 2004; 109:76-84.

The invention is further described by the following numbered paragraphs:

1. Parvovirus for use in a method for the treatment of a mesenchymal tumor.
2. The parvovirus according to paragraph 1 for the use according to paragraph 1, wherein said mesenchymal tumor is a bone tumor.
3. The parvovirus according to paragraph 1 for the use according to paragraph 2, wherein said bone tumor is a sarcoma or a metastasized tumor.
4. The parvovirus according to paragraph 1 for the use according to paragraph 2, wherein said sarcoma is an osteosarcoma or Ewing's sarcoma.
5. The parvovirus according to paragraph 1 for the use according to any one of paragraphs 1 to 4, wherein the cells of said mesenchymal tumor are (a) resistant to chemotherapy or radiotherapy, or (b) potentially relapsing tumor cells.
6. The parvovirus according to paragraph 1 for the use according to any one of paragraphs 1 or 5, wherein said parvovirus is a rodent parvovirus.
7. The parvovirus according to paragraph 6 for the use according to any one of paragraphs 1 to 5, wherein said rodent parvovirus is LuIII, Mouse minute virus (MMV), Mouse parvovirus (MPV), Rat minute virus (RMV), Rat parvovirus (RPV), Rat virus (RV) or H1 (H1PV).
8. The parvovirus according to any one of paragraphs 1 to 7 for the use according to any one of paragraphs 1 to 5, wherein said parvovirus is administered by intravenous (i.v.) intratumoral or endobronchial administration.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the treatment of a Ewing's sarcoma comprising administering a parvovirus H1 (H1PV) to the tumor.

2. The method according to claim 1, wherein the cells of said Ewing's sarcoma are (a) resistant to chemotherapy or radiotherapy, or (b) potentially relapsing tumor cells.

3. The method according to claim 1, wherein said parvovirus is administered by intravenous (i.v.), intratumoral or endobronchial administration.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="primer NS1-FOR"
      /organism="artificial sequences"

<400> SEQUENCE: 1
gcgcggcaga attcaaact                                              19

<210> SEQ ID NO 2
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer NS1-REV"
      /organism="artificial sequences"

<400> SEQUENCE: 2
ccacctggtt gagccatcat                                             20

<210> SEQ ID NO 3
<211> LENGTH: 17
<212> TYPE: DNA
<213> ORGANISM: artificial sequences
<220> FEATURE:
<221> NAME/KEY: source
<222> LOCATION: 1..17
<223> OTHER INFORMATION: /mol_type="DNA"
      /note="NS1-specific probe"
      /organism="artificial sequences"

<400> SEQUENCE: 3
atgcagccag acagtta                                                17
```